United States Patent [19]

Vaillancourt

[11] Patent Number: 4,798,597

[45] Date of Patent: Jan. 17, 1989

[54] FLEXIBLE COMPOSITE INTUBATION TUBE

[76] Inventor: Vincent L. Vaillancourt, 30A Ridgedale Ave., East Hanover, N.J. 07936

[21] Appl. No.: 43,865

[22] Filed: Apr. 29, 1987

[51] Int. Cl.⁴ .................................. A61M 25/00
[52] U.S. Cl. ................................. 604/270; 604/265
[58] Field of Search .............. 604/21, 27, 48, 54, 604/96, 265, 266, 264, 270, 275, 280

[56] References Cited

U.S. PATENT DOCUMENTS

| | | | |
|---|---|---|---|
| 3,566,874 | 3/1971 | Shepherd et al. | 604/265 |
| 3,625,741 | 12/1971 | Stoy et al. | 604/265 |
| 3,695,921 | 10/1972 | Shepherd et al. | 604/280 |
| 3,746,683 | 7/1973 | Salyer et al. | 604/280 |
| 3,861,396 | 1/1975 | Vaillancourt | 604/129 |
| 4,026,296 | 5/1977 | Stoy et al. | 604/96 |
| 4,373,009 | 2/1983 | Winn | 604/280 |
| 4,410,320 | 10/1983 | Pykstra et al. | 604/270 |
| 4,585,666 | 4/1986 | Lambert | 604/280 |
| 4,705,709 | 11/1987 | Vaillancourt | 604/265 |

FOREIGN PATENT DOCUMENTS 0136064  10/1980  Japan .................................. 604/266

Primary Examiner—Dalton L. Truluck
Attorney, Agent, or Firm—Kenyon & Kenyon

[57] ABSTRACT

The composite intubation tube has an outer pliable outer layer of plastic material and an inner concentric layer made of a hydrophilic polymer which becomes very soft and flexible in a wetted state. After intubation in a patient, a flow of gastric fluids or an inflow of nutrient solution wets the inner layer to become very soft so that pressure points on the tissue of the patient are eliminated.

16 Claims, 1 Drawing Sheet

FLEXIBLE COMPOSITE INTUBATION TUBE

This invention relates to a flexible composite intubation tube.

Heretofore, various types of intubation tubes have been known for introducing or removing fluid materials from a medical patient. For example, in the case of a gastric feeding tube, the tube is usually inserted through the nose and esophagus into the stomach of the patient and left in place for subsequent feeding of nutrient into the patient. Examples of such tubes are described in U.S. Pat. Nos. 4,249,535; 4,410,320; 4,547,192 and 4,610,673.

Generally, the tubes must have sufficient rigidity in order to be inserted into the patient while at the same time not causing damage to the internal passages within the patient. In order to achieve these purposes, it has been known to use a stylet with a collapsible tube so that the stylet can be used to introduce the tube and thereafter removed in order to leave the tube in place. However, in such cases, the use of a stylet has raised the risk of damaging the internal passages and/or organs, such as a lung of a patient, particularly where the internal passages have bends. Further, the use of a stylet normally requires the attendance of a physician in order to ensure that the tube is properly intubated.

In other cases, it has been proposed to eliminate the need for a stylet so as to avoid the attendant risks. For example, as suggested in U.S. Pat. No. 4,610,673, it is proposed to provide a feeding tube which is comprised of an elongated shaft portion and an intermediate portion which extends from a distal end to the shaft as well as a weighted bolus at the distal end. The shaft is to be constructed to have sufficient flexibility to pass the nostril of a patient but with sufficient rigidity to permit intubation without the use of a stylet. The intermediate portion is to be constructed with an enlarged dimension relative to the shaft while being provided with a transverse slot to define an inner passage and a pair of side apertures for passing feeding formula to the exterior. The intermediate portion is also to be constructed to be at least as rigid as the shaft and sufficiently flexible to permit passage through a nostril of patient during installation but nevertheless sufficiently rigid to permit installation without the use of a stylet.

As is known, the nasal passages and esophagal passages as well as the intestinal passages of a patient have numerous bends. Hence, when a feeding tube is inserted, the tube flexes around such bends and places pressure at the contact points with the passage walls. Over a period of time, which periods may be relatively short, the pressure points create a risk of necrosis of the pressured tissue. In order to avoid subsequent infection, it is necessary, from time-to-time, to remove the feeding tubes to reduce or eliminate the risk of infection.

Accordingly, it is an object of the invention to provide a feeding tube which can remain in place for relatively long periods of time.

It is another object of the invention to reduce or eliminate pressure points on the passage walls of a patient by an intubated tube.

It is another object of the invention to provide a feeding tube which can be non-rigidified after intubation.

It is another object of the invention to provide a feeding tube which is rigid when being intubated and non-rigid after being intubated.

Briefly, the invention provides a flexible composite intubation tube which is comprised of an outer layer of plastic material which is characterized in being pliable and an inner concentric layer of plastic material which defines a flow path or lumen for a fluid and which is made of a hydrophilic polymer which is characterized in being stiff in a dry state and in being very soft and flexible in a wetted state.

The tube is of a unitary construction in that the concentric layers are co-extruded. Further, the tube is of a uniform outside diameter from the proximal end to the distal end. The lumen provided by the inner layer is of standard size. For example, the inner layer may have an inner diameter of 0.08 inches in order to provide a lumen for use of the tube as a naso-gastric feeding tube.

In one embodiment, the inner layer has an inner diameter of 0.080 inches while the outer layer has an outer diameter of 0.113 inches. In addition, the inner layer is made of a thickness of 0.011 inches. In another embodiment, the inner layer may have an inner diameter of 0.080 inches and a thickness of 0.006 inches so that the outer diameter is 0.092 inches.

The outer layer of the tube may be made of any suitable pliable plastic material to cooperate with the inner layer in order to contain the inner layer, be pliable and flexible and have sufficient body to prevent tube bursting during normal syringe fluid injection. For example, the outer layer may be made of a polyether polyurethane resin while the inner layer is made of a polyurethane resin containing glycol chains.

The outer layer is selected to be compatible with body tissue and have softness and flexibility properties. The outer layer must not burst under normal syringe fluid injection conditions and have good tensile strength. Materials which satisfy these requirements include polyurethanes and, in particular, a thermoplastic elastomer supplied by the Upjohn Co. of Kalamazoo, Mich. under the name Pellethane.

The combination of a soft outer polyurethane layer or jacket made from a soft material with a Durometer of from 60 A to 80 A (Shore A scale) and a thickness one-third (⅓) to two thirds (⅔) that of a conventional tube coupled with a hydrophilic polyurethane inner core having extremely low stiffness when hydrated produces a composite tube which can not support itself thus virtually eliminating pressure points between the tube and the human body when in use.

The presence of the hydrated hydrophilic polyurethane inner core causes the composite tube to behave very much like a substantially lower Durometer tube than a tube made of a Durometer of the outer layer. For the examples given, the composite hydrated tube could not support its own weight and behaved very much like a "wet noodle". A more extended polyurethane material having a Durometer of 50 A exhibits apparent greater stiffness properties on a comparison basis.

When in use, the tube may be inserted through the nasal passage of a patient without a stylet and subsequently passed through the esophageal passages and intestinal passages as required for placement, for example in the stomach or in the small intestine as required. Once the tube has been put in place, any gastric fluids which move through the tube or any fluid nutrient solution passed through the tube for the feeding of the patient will wet the walls of the lumen of the inner hydrophilic layer. This causes the inner layer to swell while at the same time causing the inner layer to become very soft and flexible. However, it has been found that the swelling of the inner layer does not close the lumen so that fluid may still flow through the tube in either direction, as required. At same time, the overall tube becomes very soft and pliable so that the resistance to bending is substantially eliminated. In a sense, the "memory" of the plastic material is erased. As a result, the tube conforms to the bends and shape of the passages in which the tube is inserted so as to avoid pressing on the walls of the passages.

Because of the softened nature of the tube after intubation, the tube may be left in place for relatively long periods of time. More importantly, tube pressure against tissue is substantially eliminated thus increasing patient comfort and product acceptance.

These and other objects and advantages of the invention will become more apparent from the following detailed description taken in conjunction with the accompanying drawings wherein.

FIG. 1 schematically illustrates a naso-gastric tube constructed in accordance with the invention and placed in a patient:

Figures 4, 5:
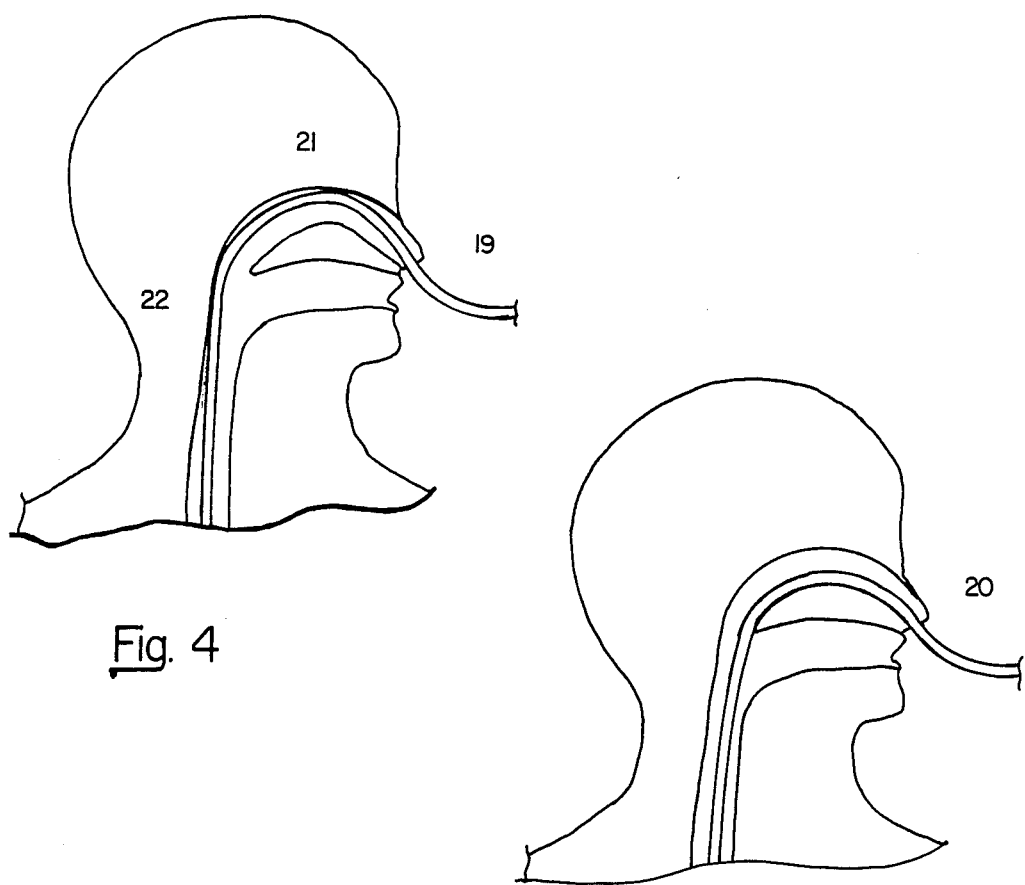

FIG. 4 schematically illustrates a prior art tube in place;

FIG. 5 schematically illustrates a tube according to the invention in place.

Figure 1:
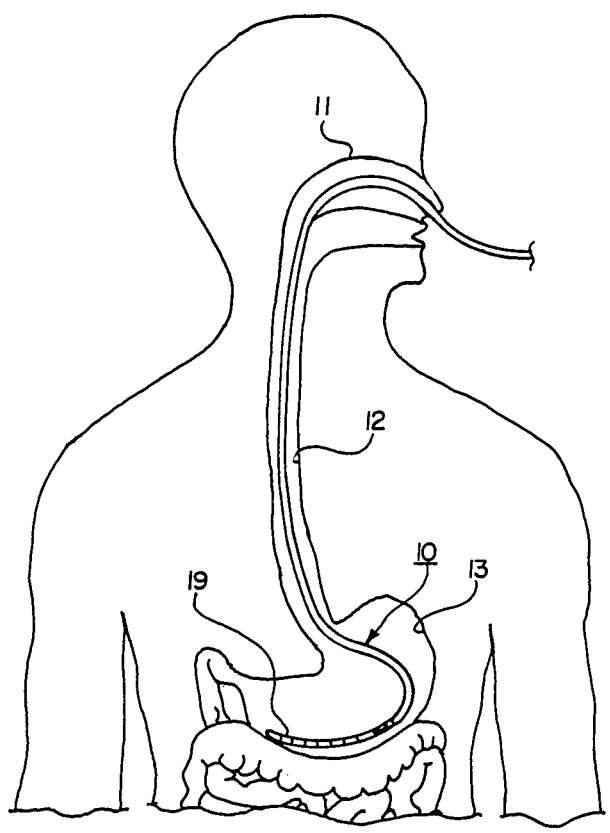

Referring to FIG. 1, the intubation tube is constructed for use as a naso-gastric tube 10 for intubation within the nasal passages 11, esophagus 12 and stomach 13 of a patient. As indicated, the tube 10 follows the tortuous path defined by the nasal passages 11, esophagus 12 and stomach 13.

Figure 2:
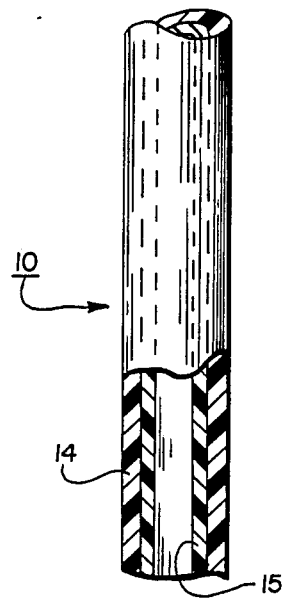
FIG. 2 illustrates an enlarged part-cross sectional view of a section of the tube of FIG. 1.

Referring to FIG. 2, the naso-gastric tube 10 is of multi-layer unitary construction. For example, the tube 10 has an outer layer 14 of plastic material which is characterized in being pliable and an inner concentric layer 15 of plastic material which defines a flow path or lumen for a fluid.

The outer layer 14 is selected for strength, toughness, clarity, toxicity properties and the like. By way of example, the outer layer is made of a polyether, polyurethane resin such as Pellethane 2363-80AE as sold by Upjohn.

The inner layer 15 is made of a hydrophilic polymer which is characterized in being stiff in a dry state and in being very soft and flexible in a wetted state. For example, the inner layer 15 is made of a polymer characterized as D-2 supplied by Tyndale Plains—Hunter, a polyurethane resin containing glycol chains to render the material hydrophilic.

The layers 14, 15 are bonded together to form an integral tube which is characterized in being sufficient pliable and self-supporting to be inserted per se into a naso-gastric passage while being soft and flexible in a wetted state within the naso-gastric passage to avoid creating pressure points therein and without closing the lumen.

Figure 3:
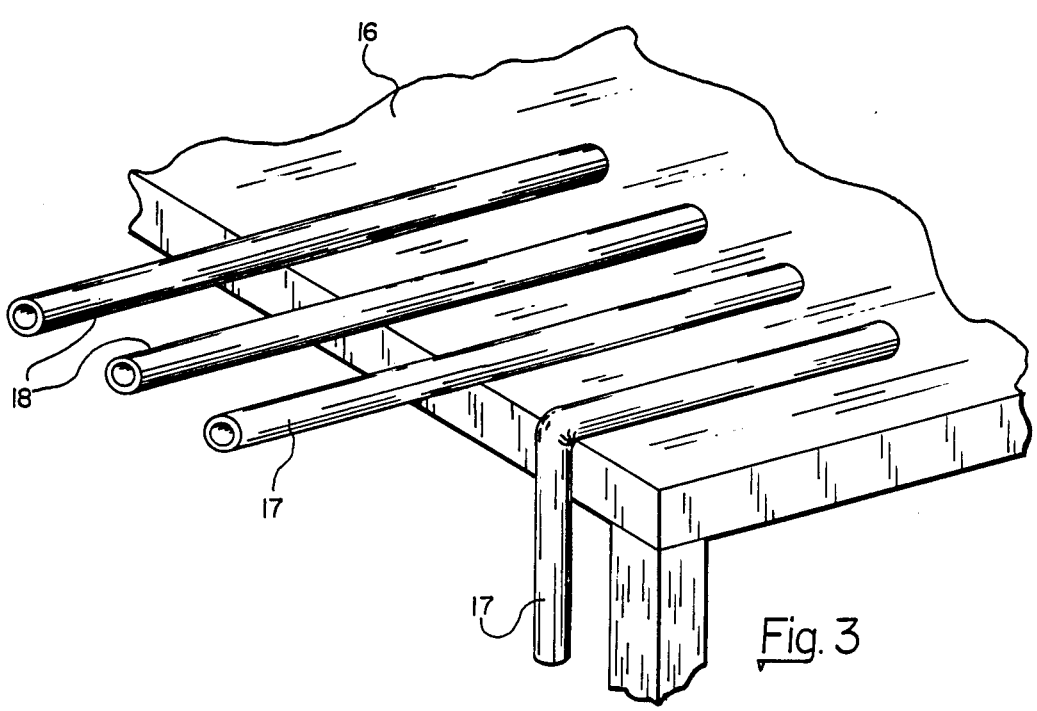
FIG. 3 illustrates a part perspective view of several sections of a tube constructed in accordance with the invention on the edge of a table.

By way of example, a tube 10 was co-extruded using a Pellethane 2363-80AE and a D-2 polymer. These materials were extruded into a tube 10 having an inner diameter of 0.080 inches and an outer diameter of 0.113 inches. The inner layer 15 also had a thickness of 0.011 inches while the outer layer 14 had a thickness of 0.0055 inches. Two sections 17 of the tube were then cut and placed on the edge of a table 16, for example as indicated in FIG. 3 and compared with sections 18 of a tube of the same outside and inside diameter which were, as extruded, rigid and would bend only with difficulty.

In addition one tube section 17 had water passed through the lumen and became flexible and would not support itself when a portion was placed beyond the edge of the table 16 as indicated. Further, the inner hydrophilic core of this tube section 17 did not buckle up and fill or otherwise obstruct the inner lumen.

By way of example, a second tube was extruded using the same materials as above. This tube also had an outside diameter of 0.113 inches and an inner diameter of 0.080 inches. However, the inner layer was of a thickness of 0.006 inches while the outer layer had a thickness of 0.0105 inches. The rigid properties of this tube in the dry state were also equivalent to those of the first example. Again, when the lumen was wetted out, the composite tube could not support its own weight.

Of note, the bond strength between the two plastic materials at the interface was exceptional for both of the examples.

Referring to FIG. 1, after intubation of the tube 10, the gastric fluids which may be withdrawn from the stomach 13 or a nutrient solution passed into the stomach 13 will wet the inner hydrophilic layer 15 causing the layer 15 to become very soft and non-self-supporting. However, the relatively thin outer layer 14 will retain its integrity while at the same time protecting the inner layer 15. The tube 10 also will become non-self-supporting and soft so that no undue pressure is placed on the various internal passageways of the patient, such as the nasal, pharynx and esophagal passageways. Thus, tissue irritation, inflammation and necrosis can be substantially reduced if not eliminated.

The tube 10 initially possesses sufficient rigidity as well as pliability so as to be inserted into a patient without the need for a stylet. As a result, the complications of a stylet are removed and a nurse may effect placement without the need for an attending physician. Accordingly, there can be a cost savings for the intubation of such tubes in a patient.

Referring to FIGS. 4 and 5, by way of comparison, a tube 19 of conventional structure and a composite tube 20 made in accordance with the invention are shown intubated in a patient. In the case of the tube 19 of prior art construction (FIG. 4), the tube 19 is pressed against the tissue at several points 21, 22 of the patient creating pressure points. However, in the case of the composite tube 20 (FIG. 5), this tube 20 being hydrated follows the contour of the patient's passages without creating pressure points.

Further, since the tube does not require any stylet, the need to provide a lubricant coating on the interior of the tube to ensure removal of a stylet is eliminated.

As indicated in FIG. 1, the tube 10 has a uniform diameter from the proximal end to the distal end. Thus, the tube can be made by simple extrusion process. Further, the tube 10 can be connected to a bolus 19, for example as described in U.S. Pat. No. 4,705,709, via a connecting member provided with suitable openings in communication with the lumen of the tube 10 in order to permit the passage of fluids from the lumen to the exterior and vice versa.

The invention thus provides an intubation tube which can be simply manufactured and which does not require a stylet for intubation. Further, the invention provides an intubation tube which is sufficiently rigid to be intubated without the need for a stylet as well as one which becomes very soft and pliable upon being wetted after intubation so as to eliminate or substantially reduce irritation and necrosis at bends within a patient's passages.

I claim:

1. A flexible composite intubation tube for connection to a bolus comprising a relatively thin outer layer of plastic material characterized in being pliable and flexible; and an inner concentric layer of plastic material defining a flow path for a fluid, said inner layer having an inner diameter of 0.080 inches and being made of a hydrophilic polymer characterized in being stiff in a dry state and in being very soft and flexible in a wetted state; said layers forming a tube characterized in being sufficiently pliable and self-supporting to be inserted per se into a naso-gastric passage and in being soft and flexible in a wetted state within the naso-gastric passage to avoid creating pressure points therein and without closing said lumen.

2. A composite intubation tube as set forth in claim 1 wherein said layer are co-extruded to form a unitary construction.

3. A composite intubation tube as set forth in claim 1 wherein said outer layer has an outer diameter of 0.113 inches.

4. A composite intubation tube as set forth in claim 3 wherein said inner layer has a thickness of 0.011 inches.

5. A composite intubation tube as set forth in claim 3 wherein said outer layer is made of a polyether polyurethane resin and said inner layer is made of a polyurethane resin containing glycol chains.

6. A composite intubation tube as set forth in claim 3 wherein said inner layer has a thickness of 0.006 inches.

7. A composite intubation tube as set forth in claim 1 wherein said outer layer is made of a polyether polyurethane resin and said inner layer is made of a polyurethane resin containing glycol chains.

8. A naso-gastric tube for connection to a bolus comprising a soft outer layer of plastic material of pliable and flexible nature having sufficient body to prevent tube bursting during syringe fluid injection; and an inner concentric layer within said outer layer, said inner layer defining a lumen for fluid passage and being made of a plastic hydrophilic material characterized in being stiff in a dry state to permit insertion of the tube into a naso-gastric passage and in being very soft and flexible in a wetted state within the naso-gastric passage to render the tube non-self supporting without closing said lumen to eliminate pressure points in the passage.

9. A naso-gastric tube as set forth in claim 8 wherein said outer layer is made of a polyether polyurethane resin and said inner layer is made of a polyurethane resin containing glycol chains.

10. A naso-gastric tube as set forth in claim 9 wherein said inner layer has an inner diameter of 0.080 inches and said outer layer has an outer diameter of 0.113 inches.

11. A naso-gastric tube as set forth in claim 10 wherein said inner layer is of a greater thickness than said outer layer.

12. A naso-gastric tube as set forth in claim 8 herein said outer layer has a Durometer of from 60 A to 80 A (Shore A scale).

13. A naso-gastric tube for connection to a bolus comprising a relatively thin soft outer layer of pliable and flexible material;

an inner concentric layer of hydrophilic material defining a lumen for passage of a fluid; and said layers being bonded together to form an integral tube characterized in being sufficiently pliable and self-supporting to be inserted per se into a naso-gastric passage and in being soft and flexible in a wetted state within the naso-gastric passage to avoid creating pressure points therein and without closing said lumen.

14. A naso-gastric tube as set forth in claim 13 wherein said inner layer has an inner diameter of 0.080 inches and said outer layer has an outer diameter of 0.113 inches.

15. A naso-gastric forth in claim 13 wherein said outer layer is made of a polyether polyurethane resin and said inner layer is made of a polyurethane resin containing glycol chains.

16. A naso-gastric tube as set forth in claim 12 wherein said outer layer has a Durometer of from 60 A to 80 A (Shore A scale).

* * * * *

UNITED STATES PATENT AND TRADEMARK OFFICE
CERTIFICATE OF CORRECTION

PATENT NO.  : 4,798,597
DATED       : January 17, 1989
INVENTOR(S) : Vincent L. Vaillancourt It is certified that error appears in the above-identified patent and that said Letters Patent is hereby corrected as shown below:

On The Title Page insert:  -- [73] Assignee: Sherwood Medical Company, St. Louis, Missouri --.

```
Column 3, line 56 change "sufficient" to -sufficiently-
Column 5, line 23 change "layer" to -layers-
Column 6, line 19 change "herein" to -wherein-
```

Signed and Sealed this

Twenty-fourth Day of October, 1989

Attest:

DONALD J. QUIGG

Attesting Officer

Commissioner of Patents and Trademarks